United States Patent [19]

Chao et al.

[11] Patent Number: 4,982,015

[45] Date of Patent: Jan. 1, 1991

[54] PROCESS FOR THE OXIDATION OF BENZENE TO PHENOL

[75] Inventors: Kuo-Hua Chao; Raymond T. Moy, both of Houston, Tex.

[73] Assignee: Shell Oil Company, Houston, Tex.

[21] Appl. No.: 412,757

[22] Filed: Sep. 26, 1989

[51] Int. Cl.⁵ .............................................. C07C 37/58
[52] U.S. Cl. .................................... 568/802; 568/741; 568/771; 568/800
[58] Field of Search ................. 568/741, 771, 802, 800

[56] References Cited

U.S. PATENT DOCUMENTS 3,172,917  3/1965  Dundee et al. ................... 568/802

Primary Examiner—Werren B. Lone

[57] ABSTRACT

The instant invention relates to a process for the oxidation of benzene to phenol which comprises contacting benzene and molecular oxygen with a dihydrodihydroxynaphthoquinone, optionally in the presence of an oxidation catalyst, and subsequently separating from the reaction product phenol and the corresponding naphthoquinone. The by-product napththoquinone is suitably recycled to the benzene oxidation step by hydrogenating the naphthoquinone to the dihydrodihydroxynapththoquinone.

12 Claims, No Drawings

PROCESS FOR THE OXIDATION OF BENZENE TO PHENOL

FIELD OF THE INVENTION

This invention relates to a process for the oxidation of benzene to phenol using molecular oxygen.

BACKGROUND OF THE INVENTION

Phenol is a widely used chemical intermediate. Two major uses are phenolic resins and bisphenol A. Currently, phenol is produced primarily using the cumene process. Additional technologies such as toluene oxidation, benzene sulfonation/hydrolysis, benzene chlorination/hydrolysis and cyclohexane oxidation/dehydrogenation processes are also available, although currently they are not as economically competitive as the cumene process. While the cumene process does use oxygen to convert cumene to cumene hydroperoxide, it does have the disadvantage of producing a mole of by-product acetone for each mole of phenol produced. None of the other technologies noted above use air or oxygen to directly oxidize benzene to phenol. The direct oxidation of benzene using air or oxygen is more desirable than using other more expensive oxidants like hydrogen peroxide and would also result in less by-product make.

SUMMARY OF THE INVENTION

The instant invention relates to a process for the oxidation of benzene to phenol which comprises contacting and thereby reacting benzene and oxygen with a dihydrodihydroxynaphthalene substituted with at least one electron-withdrawing substituent group, optionally in the presence of an oxidation catalyst, and subsequently separating from the reaction product phenol and the corresponding napthoquinone. The by-product naphthoquinone is suitably recycled to the benzene oxidation step by hydrogenating the naphthoquinone to the corresponding dihydrodihydroxynaphthalene by contacting it with hydrogen in the presence of a hydrogenation catalyst.

DETAILED DESCRIPTION OF THE INVENTION

The instant process comprises reacting benzene with molecular oxygen to produce phenol in the presence of an oxygen activator which promotes the reaction, optionally in the presence of an oxidation catalyst.

The process makes use of a recyclable oxygen activator. This activator activates oxygen thereby causing it to react with benzene and thus converting it to phenol while at the same time the activator is concomitantly oxidized. The oxidized activator ("activator-precursor") is then reduced with hydrogen back to its original state and recycled back to the benzene oxidation step.

The oxygen activator-precursor utilized herein is naphthoquinone, that is 1,4-dihydro-1,4-diketonaphthalene and/or 1,2-dihydro-1,2-diketonaphthalene, substituted with at least one electron-withdrawing substituent group. Electron-withdrawing substituent groups are well known to those skilled in the chemical arts and include by way of non-limiting examples $-N(CH_3)_3{}^+$, $-NO_2$, $-CN$, $-SO_3H$, $-SO_3$, $-COOH$, $-COO^+$, $-CHO$, $-X$ (halo), $-OCF_3$, etc. The particular substituent utilized should be inert under the reaction conditions and relatively small, such that it does not provide so much steric hindrance that the oxygen activation reaction step is inhibited. Suitable substituted naphthoquinones can be determined by routine experimentation. The oxygen activator-precursor is usually more readily obtained or synthesized than is the oxygen activator, and typically the activator is obtained by reducing the activator-precursor with hydrogen in the presence of a reducing catalyst. In effect, the instant process utilizes an oxidation/reduction cycle to recycle an oxygen activator comprising 1,4-dihydro-1,4-dihydroxynaphthalene and/or 1,2-dihydro-1,2-dihydroxynaphthalene to the corresponding activator-precursor comprising 1,4-dihydro1,4-diketonaphthalene and/or 1,2-dihydro-1,2-diketonaphthalene and back again.

The oxygen activator may be utilized in a one phase hydrocarbon system or in a two phase hydrocarbon/water system. The solubility of the activator in the aqueous phase will depend on the presence of water solubilizing substituents on the activator, such as sulfonate substituent(s), particularly the alkali metal sulfonates. The use of a two phase system can have certain processing advantages, particularly when the activator is more soluble in the aqueous phase than in the hydrocarbon phase. In the latter case the organic phase contains the unreacted benzene and the major portion of the produced phenol and the aqueous phase contains the oxygen activator and activator-precursor and a residual amount of product phenol, which will allow a ready separation of product phenol and reactant benzene from the oxygen activator/precursor.

When utilizing the two phase system, the presence of basic conditions in the aqueous phase during the oxidation reaction has been found to inhibit the oxidation of benzene to phenol. Thus, it is desired to maintain the pH of the aqueous phase below about 7 during the reaction. Preferably the pH is maintained between about 1 to about 5. The desired pH may be obtained by adding a suitable amount of an organic acid, such as sulfuric or hydrochloric acid, to the aqueous phase. Buffering salts may also be utilized. However, high concentrations of salts lower the yield of phenol.

Molecular oxygen is utilized to oxidize the benzene to phenol. While pure oxygen can be utilized, it does pose problems with flammability and more dilute concentrations of oxygen are preferably utilized. Preferably air is utilized as the source of molecular oxygen.

An oxidation catalyst is optionally utilized in the reaction to oxidize benzene to phenol. The use of an oxidation catalyst has been found to enhance the rates of reaction. The oxidation catalysts utilized in the instant process are traditional oxidation catalysts used in the art to oxidize organic compounds. Non-limiting examples of these oxidation catalysts comprise vanadium, chromium, manganese, iron, cobalt, copper, yttrium, niobium, molybdenum, ruthenium, rhodium, palladium, silver, the lanthanide series, rhenium, osmium, bismuth, thorium, uranium, tungsten, mercury, lead, titanium, thallium, etc. The oxidation catalyst may be homogeneous or heterogeneous. When the catalyst is homogeneous, it is preferred that the catalyst be soluble in the aqueous phase in order to facilitate separation of the catalyst from the product phenol concentrated in the organic phase. A preferred homogeneous catalyst is a water soluble ferric salt, particularly ferric nitrate or ferric chloride. Heterogeneous catalysts are preferred as they are readily separated from unreacted feed and product. Preferred is palladium dispersed on an inert support such as carbon or alumina.

The benzene oxidation reaction may be carried out in a batch reactor or in a continuous flow reactor. For example, it may be carried out in a fixed bed reactor, the bed comprising the catalyst, wherein benzene and the oxygen activator is passed over the bed in the presence of an oxygencontaining gas. Alternatively, benzene and the oxygen activator may be trickled over a bed of inert support materials, such as alumina raschig rings or berl saddles, in the presence of an oxygen-containing gas and optionally in the presence of a homogenous oxidation catalyst. Other continuous reactor configurations will be readily apparent to one skilled in the art.

Batch reactors, such as autoclaves, are also suitable. For example, benzene, an aqueous solution of the oxygen activator and optionally an oxidation catalyst can be loaded into an autoclave, the autoclave sealed and charged with an oxygen-containing gas, heated to a desired reaction temperature and the reaction allowed to proceed.

Reaction pressures for the instant process are not critical and will typically range from about atmospheric to about 100 atmospheres, although higher and lower pressures can be utilized. The reaction temperature of the instant process depends, inter alia, upon the particular optional oxidation catalyst utilized, but will typically range from about 0° C. to about 100° C., preferably from about 25° C. to about 75° C.

For the two phase system, after reaction there will be an hydrocarbon phase containing unreacted benzene and the major portion of the product phenol. The hydrocarbon phase may be diluted with a inert organic solvent, such as an alkane. There will also be an aqueous phase containing the oxidized oxygen activator, a small amount of phenol and the optional oxidation catalyst if it is homogeneous. The hydrocarbon phase is processed, say by distillation, to recover the product benzene. The aqueous phase may also be processed to remove any residual phenol, say by liquid-liquid extraction with an organic solvent.

For the single phase hydrocarbon system, after reaction, the hydrocarbon phase is processed by conventional techniques such as distillation, liquid-liquid extraction with water, filtration, etc., in order to separate the product phenol, the oxidized activator, unreacted benzene and any optional oxidation catalyst.

It is a particular advantage of the instant process that the aqueous phase from the benzene oxidation reaction containing the oxidized oxygen activator can be reduced by contact with hydrogen and a hydrogenation catalyst to regenerate the oxygen activator. The regenerated oxygen activator can then be conveniently recycled to the benzene oxidation reactor. The hydrogenation catalyst used to reduce the oxidized oxygen activator can be any of the conventional hydrogenation catalysts that are useful for hydrogenating organic compounds. Non-limiting examples of these hydrogenation catalysts comprise iron, cobalt, nickel, copper, silver, osmium, platinum, palladium, rhodium, ruthenium, tin, iridium, mercury, etc. The hydrogenation catalyst may be homogeneous or heterogeneous. However, a heterogeneous catalyst is preferred since it can more readily be separated from the regenerated oxygen activator prior to its recycle to the benzene oxidation reactor. A preferred catalyst is palladium dispersed on an inert support such as carbon or alumina. Reaction pressures for the hydrogenation are not critical and will typically range from about atmospheric to about 100 atmospheres, although higher and lower pressures can be utilized. The reaction temperature will depend upon the particular hydrogenation catalyst utilized, but will typically range from about 0° C. to about 100° C., preferably from about 255° C. to about 75° C. Under certain conditions the hydrogenation catalyst can also serve as the optional oxidation catalyst.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

Illustrative Embodiment I

Part A: Preparation of the Oxygen Activator

First, 3.65 mmol of sodium 1,2-napththoquinone-4-sulfonate was added to a 100 milliliter stainless steel autoclave which contained a mixture of 20 milliliters of water and 200 milligrams of 5% palladium dispersed on carbon (Catalyst CP-41, supplied by Engelhard). The autoclave was flushed with hydrogen gas three times and then filled with hydrogen gas at 45 psig. The pressure was allowed to drop to zero as the reaction was carried out. The reaction product was removed and filtered to separate out the catalyst.

Part B: Air Oxidation of Benzene along with 10 milliliters of benzene. The autoclave was sealed, charged with air at 150 psig and then heated to about 50° C. for about four hours. After cooling the autoclave, the organic layer was separated and combined with diethy ether extractions of the aqueous layer. Analysis showed that the phenol yield was 3% (based on the naphthoquinone) and that the selectivity to phenol was greater than 95%.

Illustrative Embodiment II

Illustrative Embodiment was repeated except that 0.242 grams of ferric nitrate was added to the autoclave as cocatalyst. Analysis of the reaction product showed that the phenol yield was 3% (based on the naphthoquinone) and that the selectivity to phenol was greater than 95%. The rate of reaction of Illustrative Embodiment II was estimated to be about four times the rate of reaction of Illustrative Embodiment I.

Illustrative Embodiment III 3.65 Mmol of sodium 1,2-naphthoquinone-4-sulfonate was added to a 100 milliliter stainless steel autoclave which contained a mixture of 20 milliliters of water, 10 milliliters of benzene and 200 milligrams of 5% palladium dispersed on carbon (Catalyst CP-41, supplied by Engelhard). The autoclave was flushed with hydrogen gas three times and then filled with hydrogen gas at 45 psig. The pressure was allowed to drop to zero as the reaction was carried out. The autoclave was then charged with air at 150 psig and then heated to about 50° C. for about four hours. After cooling the autoclave, the organic layer was separated and combined with diethy ether extractions of the aqueous layer. Analysis showed that the phenol yield was 3% (based on the anthraquinone) and that the selectivity to phenol was greater than 95%.

Illustrative Embodiment IV

The process of Illustrative Embodiment II was repeated with the exception that different naphthoquinones were utilized. The results of these experiments are shown in FIG. 1 below.

| Precursor Compound | Cocatalyst | Yield of Phenol |
|---|---|---|
| 1,4-naphthoquinone | None | 0% |
| 2.3-dichloro-1,4-naphthoquinone | Fe(NO$_3$)$_3$ | 1.0% |
| 2-chloro-3-morpholino-1,4-naphthoquinone | Fe(NO$_3$)$_3$ | 3.0% |

We claim:

1. A process for the oxidation of benzene to phenol which comprises contacting at a temperature ranging from about 0° C. to about 100° C. benzene and molecular oxygen with dihydrodihydroxynaphthalene substituted with at least one electron-withdrawing substituent group selected from -N(CH$_3$)$_3$+, -NO$_2$, -CN, -SO$_3$H, -SO$_3^{30}$, -COOH, -COO+, -CHO, -X(halo) and -OCF$_3$, and subsequently separating from the reaction product phenol and the corresponding naphthoquinone.

2. The process of claim 1 wherein the oxidation is carried out at a temperature ranging from about 25° C. to about 75° C.

3. The process of any one of claims 1-2 wherein the oxidation is also carried out in the presence of an oxidation catalyst comprising vanadium, chromium, manganese, iron, cobalt, copper, yttrium, niobium, molybdenum, ruthenium, rhodium, palladium, silver, the lanthanide series, rhenium, osmium, bismuth, thorium, uranium, tungsten, mercury, lead, titanium and/or thallium.

4. The process of claim 3 wherein an aqueous phase is present and the oxidation catalyst is a water soluble ferric salt selected from ferric nitrate, ferric chloride and mixtures thereof.

5. The process of claim 3 wherein the oxidation catalyst is a supported palladium catalyst.

6. The process of claim 5 wherein the oxidation catalyst is palladium supported on carbon.

7. The process of any one of claim 1-2 wherein the naphthoquinone is contacted with hydrogen and hydrogenation catalyst whereby the anthraquinone is hydrogenated to the corresponding dihydrodihydroxynaphthoquinone which is then recycled back to the oxidation reaction.

8. The process of claim 7 wherein the oxidation is also carried out in the presence of an oxidation catalyst comprising vanadium, chromium, manganese, iron, cobalt, copper, yttrium, niobium, molybdenum, ruthenium, rhodium, palladium, silver, the lanthanide series, rhenium, osmium, bismuth, thorium, uranium, tungsten, mercury, lead, titanium and/or thallium.

9. The process of claim 8 wherein an aqueous phase is present and the oxidation catalyst is a water soluble ferric salt selected from ferric nitrate, ferric chloride and mixtures thereof.

10. The process of claim 8 wherein the oxidation catalyst is a supported palladium catalyst.

11. The process of claim 10 wherein the oxidation catalyst is palladium supported on carbon.

12. The process of claim 1 wherein the electron-withdrawing substituent is selected from halo or sulfonate.

* * * * *